US00PP11058P

United States Patent [19]

Oliver

[11] Patent Number: Plant 11,058

[45] Date of Patent: Sep. 14, 1999

[54] HEUCHERA PLANT NAMED 'PETITE PEARL FAIRY'

[76] Inventor: Charles G. Oliver, R.D. 2, Box 110, Scottdale, Pa. 15683

[21] Appl. No.: 09/005,619

[22] Filed: Jan. 12, 1998

[51] Int. Cl.[6] ..... A01H 5/00

[52] U.S. Cl. ..... Plt./263

[58] Field of Search ..... Plt./68.1, 263

*Primary Examiner*—Howard J. Locker
*Assistant Examiner*—Kent L. Bell
*Attorney, Agent, or Firm*—C. A. Whealy

[57] ABSTRACT

A distinct cultivar of Heuchera plant named 'Petite Pearl Fairy', characterized by its compact plant form; attractive marbled foliage with dark green to gray veins and silver interveinal areas which fade to green-bronze in the summer; loosely ruffled leaf margins; numerous showy and large flowers; compact, narrow and uniform flowering stems; and excellent garden performance.

1 Drawing Sheet

The present invention relates to a new and distinct cultivar of Heuchera, botanically known as Heuchera sp., and hereinafter referred to by the cultivar name 'Petite Pearl Fairy'.

The new cultivar is a product of a planned breeding program conducted by the inventor in Scottdale, Pa. The objective of the breeding program is to create new miniature garden-type Heuchera cultivars with attractive foliage, showy flowers, and good garden performance.

The new cultivar was selected by the inventor from seedling progeny from a cross made in 1994 by the inventor of the Heuchera sp. cultivar 'SanPico Rosita' (not patented) as the male or pollen parent with the Heuchera sp. cultivar 'Regina' (not patented) as the female or seed parent. The new cultivar was selected by the inventor at his nursery in Scottdale, Pa. from these seedlings.

Asexual reproduction of the new cultivar by divisions and by shoot cuttings taken at Scottdale, Pa., has shown that the unique features of this new Heuchera plant are stable and reproduced true to type in successive generations of asexual reproduction.

In side-by-side comparisons in Scottdale, Pa., under commercial practice, plants of the new Heuchera are different from plants of the male parent, the alpine-type cultivar 'SanPico Rosita' in the following characteristics:

1. Plants of the new Heuchera have slightly longer flowering stems than plants of the cultivar 'SanPico Rosita'.
2. Leaves of plants of the new Heuchera are marbled with dark green to gray veins and silver interveinal areas whereas leaves of plants of 'SanPico Rosita' are solid green.
3. Leaf margins of plants of the new Heuchera are loosely ruffled whereas leaf margins of plants of 'SanPico Rosita' are not ruffled.

In side-by-side comparisons in Scottdale, Pa., under commercial practice, plants of the new Heuchera are different from plants of the female parent, the cultivar 'Regina' in the following characteristics:

1. Plants of the new Heuchera are compact, miniature form, whereas plants of the cultivar 'Regina' are full-size.
2. Leaves of plants of the new Heuchera are marbled with dark green to gray veins and silver interveinal areas which fade to green-bronze in the summer whereas leaves of plants of the cultivar 'Regina' are purple-bronze and do not fade in the summer. In addition, foliage markings on plants of the new Heuchera are less defined compared to plants fo the Heuchera 'Regina'.
3. Leaves of plants of the new Heuchera lack the metallic sheen during the autumn and winter that is present on leaves of plants of the cultivar 'Regina'.

4. Leaf margins of plants of the new Heuchera are loosely ruffled whereas leaf margins of plants of 'Regina' are not ruffled.
5. Inflorescences of plants of the new Heuchera are shorter, narrower and more uniform than inflorescences of plants of the cultivar 'Regina'. In addition, plants of the new Heuchera have more flowering stems than plants of the cultivar 'Regina'.

The following traits have been repeatedly observed and are determined to be the unique characteristics of 'Petite Pearl Fairy'. These characteristics in combination distinguish the new Heuchera plant as a new and distinct cultivar:

1. Compact plant form.
2. Marbled foliage with dark green to gray veins and silver interveinal areas which fade to green-bronze in the summer. Markings not well-defined.
3. Loosely ruffled leaf margins.
4. Numerous showy and large flowers.
5. Compact, narrow and uniform flowering stems.
6. Excellent garden performance.

The new Heuchera plant has not been observed under all possible environmental conditions. The phenotype may vary significantly with variations in environment such as temperature, light level, nutrition and water status without, however, any variance in genotype.

Plants of the new Heuchera can be compared to plants of the sibling Heuchera cultivar, 'Petite Marbled Burgundy', disclosed in U.S. Plant Patent application Ser. No. 09/005,620. In side-by-side comparisons in Scottdale, Pa., under commercial practice, plants of the new Heuchera are different from plants of the cultivar 'Petite Marbled Burgundy' in the following characteristics:

1. Plants of the new Heuchera are shorter than plants of the cultivar 'Petite Marbled Burgundy'.
2. Plants of the new Heuchera have smaller leaves and shorter petioles than plants of the cultivar 'Petite Marbled Burgundy'.
3. Plants of the new Heuchera have slightly ruffled leaf margins whereas plants of the cultivar 'Petite Marbled Burgundy' do not have ruffled leaf margins.
4. Plants of the new Heuchera have less sharply defined silver interveinal areas than plants of the cultivar 'Petite Marbled Burgundy'.
5. Plants of the new Heuchera have more inflorescences and more flowers than plants of the cultivar 'Petite Marbled Burgundy'.

Plants of the new Heuchera can be compared to plants of the species *Heuchera pulchella*, a popular species native to the Southwestern United States. In side-by-side comparisons in Scottdale, Pa., under commercial practice, plants of the new Heuchera are different from plants of the species *Heuchera pulchella* in the following characteristics:

1. Leaves of plants of the new Heuchera are marbled with dark green to gray veins and silver interveinal areas whereas leaves of plants of the species *Heuchera pulchella* are solid green.

2. Leaf margins of plants of the new Heuchera are loosely ruffled whereas leaf margins of plants of the species *Heuchera pulchella* are not ruffled.

3. Growth habit of plants of the new Heuchera is tighter and less open than the growth habit of plants of the species *Heuchera pulchella*.

Plants of the new Heuchera can be compared to plants of the nonpatented commercial cultivar 'Montrose Ruby'. In side-by-side comparisons in Scottdale, Pa., under commercial practice, plants of the new Heuchera are different from plants of the cultivar 'Montrose Ruby' in the following characteristics:

1. Plants of the new Heuchera are compact, miniature form, whereas plants of the cultivar 'Montrose Ruby' are full-size.

2. Leaf margins of plants of the new Heuchera are loosely ruffled whereas leaf margins of plants of the cultivar 'Montrose Ruby' are not ruffled.

3. Flowers of plants of the new Heuchera are showier and larger than flowers of plants of the cultivar 'Montrose Ruby'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a 18-month old plant of 'Petite Pearl Fairy'.

The photograph at the bottom of the sheet comprises a close-up view of a typical leaves of 'Petite Pearl Fairy' in September. Flower and foliage colors in the photographs may appear different from the actual colors due to light reflectance and shadows.

DETAILED BOTANICAL DESCRIPTION

The following observations, measurements, values, and comparisons described plants grown in Scottdale, Pa., in a glass-covered greenhouse with day temperatures ranging from 16 to 27° C. and night temperatures ranging from 4 to 16° C. depending upon the season. In the following description, color references are made to The Royal Horticultural Society Colour Chart except where general terms of ordinary dictionary significance are used.

Classification:

*Botanical.*—Heuchera sp. cultivar 'Petite Pearl Fairy'.

Parentage:

*Male or pollen parent.*—Heuchera sp. cv. 'SanPico Rosita' (not patented).

*Female or seed parent.*—Heuchera sp. cv. 'Regina' (not patented).

Propagation:

*Type.*—By divisions, by shoot cuttings or by tissue culture.

*Time to initiate roots.*—About 14 days at temperatures of 21° C.

*Time to develop roots.*—About 30 days at temperatures of 21 ° C.

*Rooting habit.*—Young plants, fibrous; older plants becoming thick and woody.

Plant description:

*Plant form and growth habit.*—Perennial, mounded foliage with numerous upright and strong flowering stems.

*Vigor.*—Vigorous, rapid growth rate.

*Crop time.*—From cuttings or rooted tissue-cultured plantlets, about nine months are required to produce mature flowering plants. Plants typically produced in 10-cm containers.

*Plant height, soil level to top of foliage.*—About 8 cm.

*Plant height, soil level to top of flowers.*—About 2.5 cm.

*Plant diameter.*—About 15 cm.

Foliage description:

*Arrangement.*—Rosette, single.

*Length.*—2.5 to 3.5 cm.

*Width.*—2.5 to 4 cm.

*Shape.*—Rounded cordate, 7-lobed.

*Apex.*—Broadly obtuse, lobed.

*Base.*—Cordate.

*Margin type.*—Crenate, ciliate, margins loosely ruffled.

*Venation pattern.*—Reticulate.

*Texture.*—Slightly rough, slight pubescence on lower surface.

*Color.*—Marbled foliage with dark green to gray veins and silver interveinal areas which fade to green-bronze in the summer. Markings not well-defined. Leaf color is mostly green (venation coloration) with narrow silver interveinal areas. Young foliage, upper surface: 198A. Young foliage, lower surface: 187A. Mature foliage, upper surface: 198A. Mature foliage, lower surface: 187A fading to 187D in summer. Venation, upper surface: 131A underlain with 200A, fading to 189A in summer. Venation, lower surface: Same as leaf color.

*Petiole.*—Length: About 4 cm. Diameter: About 0.15 mm. Color: 186C.

*Durability of foliage to stress.*—High.

Flower description:

*Natural flowering season.*—Spring, May through June in the Northern Hemisphere.

*Flower arrangement.*—Numerous single flowers arranged on narrow panicles; usually about 40 to 50 flowers per flowering stem. Flowering continuous; usually about 10 to 12 flowering stems per plant.

*Flower appearance.*—Campanulate, persistent. Individual flowers last about one week on plant.

*Fragrance.*—None detected.

*Flower diameter.*—About 4 mm.

*Flower depth (height).*—About 6 mm.

*Flower bud.*—Length: About 4 mm. Diameter: About 2.5 mm. Shape: Bulbous. Color: 63C. Rate of opening: About 2 to 3 days.

*Petals.*—Appearance: Thin. Texture: Slightly pubescent. Arrangement: Radially symmetrical with five petals. Shape: Spatulate. Apex: Rounded. Margin: Entire. Length: About 3 mm. Width: About 1 mm. Color: When opening, inner surface: White. When opening, outer surface: White. Fully opened, inner surface: White. Fully opened, outer surface: White.

*Sepals/calyx.*—Appearance: Five sepals fused into a radially symmetrical calyx tube. Sepal apex: Obtuse.

Sepal margin: Entire. Sepal texture: Thin, pubescent. Sepal color: 65D. Calyx length: About 5 mm. Calyx diameter: About 3.5 mm.

*Peduncles.*—Angle: Erect. Strength: Strong. Color: 187B.

*Pedicels.*—Length—About 4 mm. Angle: Horizontal to drooping. Strength: Strong. Color: 63C.

*Reproductive organs.*—Androecium: Stamen number: Five. Anther shape: Oval. Anther size: About 0.2 mm. Anther color: 20B. Amount of pollen: Moderate. Pollen color: 20B. Gynoecium: Pistil number: Two. Pistil length: About 5.5 mm. Stigma shape: Rounded. Stigma color: 157C. Style length: About 4 mm. Style color: 157C. Ovary color: 157C.

*Seed description.*—Length: About 0.6 mm. Diameter: About 0.3 mm. Color: Black.

Disease resistance: Some susceptibility to fungus and/or bacterial wilt has been observed during humid hot conditions.

It is claimed:

1. A new and distinct Heuchera plant named 'Petite Pearl Fairy', as illustrated and described.

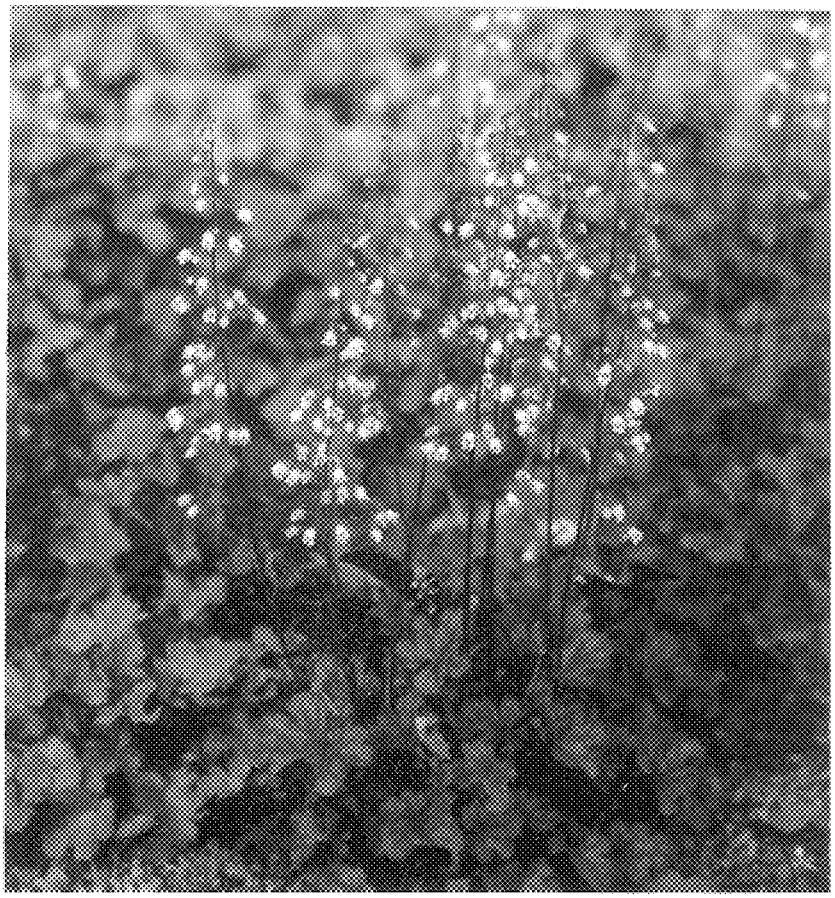
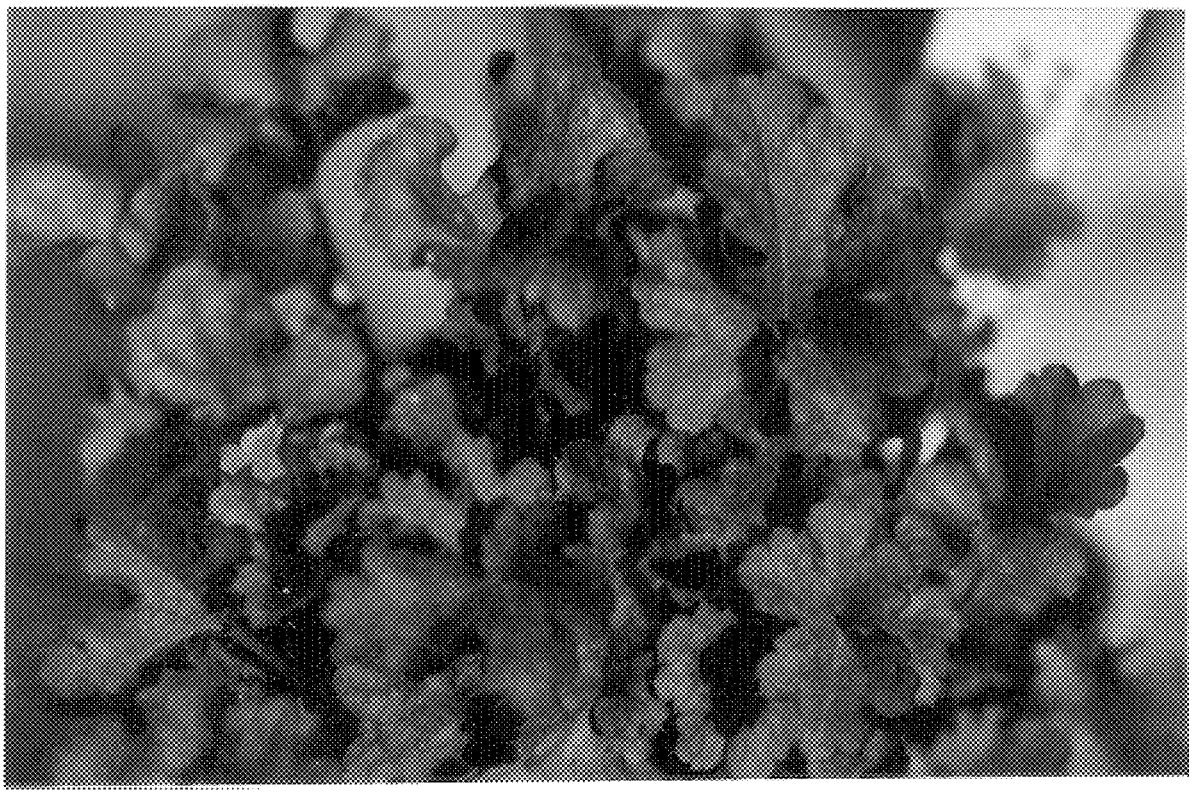

* * * * *